US012638463B2

(12) United States Patent
Kapp-Barnea

(10) Patent No.: US 12,638,463 B2
(45) Date of Patent: May 26, 2026

(54) ANALYSIS OF BODILY EMISSONS

(71) Applicant: Outsense Diagnostics Ltd., M.P. Hof Carmel (IL)

(72) Inventor: Yaara Kapp-Barnea, Nirit (IL)

(73) Assignee: Outsense Diagnostics Ltd., Or Yehuda (IL)

( * ) Notice: Subject to any disclaimer, the term of this patent is extended or adjusted under 35 U.S.C. 154(b) by 773 days.

(21) Appl. No.: 17/916,690

(22) PCT Filed: Apr. 6, 2021

(86) PCT No.: PCT/IB2021/052856
§ 371 (c)(1),
(2) Date: Oct. 3, 2022

(87) PCT Pub. No.: WO2021/205345
PCT Pub. Date: Oct. 14, 2021

(65) Prior Publication Data
US 2023/0176080 A1 Jun. 8, 2023

Related U.S. Application Data

(60) Provisional application No. 63/006,130, filed on Apr. 7, 2020.

(51) Int. Cl.
*G01N 35/00* (2006.01)
*A61B 10/00* (2006.01)
(Continued)

(52) U.S. Cl.
CPC ... *G01N 35/00584* (2013.01); *A61B 10/0038* (2013.01); *A61B 10/007* (2013.01);
(Continued)

(58) Field of Classification Search
CPC .............. A61K 49/1815; G01R 33/465; G01R 33/5601; A61B 10/0038; A61B 10/007;
(Continued)

(56) References Cited

U.S. PATENT DOCUMENTS 10,575,830 B2 3/2020 Attar
2016/0278705 A1 9/2016 Han et al.
(Continued)

FOREIGN PATENT DOCUMENTS

JP 2009204598 A 9/2009
JP 2014033921 A * 2/2014
(Continued)

OTHER PUBLICATIONS

Shimizy JP2014033921A English Translation (Year: 2025).*
(Continued)

*Primary Examiner* — Jennifer Wecker
*Assistant Examiner* — Jonathan Bortoli
(74) *Attorney, Agent, or Firm* — Husch Blackwell LLP

(57) ABSTRACT

Apparatus and methods are described for use with urine and feces of a subject that are emitted into a toilet bowl. One or more sensors are coupled to the toilet bowl and are configured to detect one or more urine-related parameters relating to the subject's urine and one or more feces-related parameters relating to the subject's feces, without requiring any action to be performed by any person subsequent to emission of the urine or feces into the toilet bowl. A computer processor determines that the subject is suffering from dehydration, at least partially based upon the one or more urine-related parameters, and classifies the dehydration as being a given type of dehydration, at least partially based upon the one or more feces-related parameters. Other applications are also described.

14 Claims, 4 Drawing Sheets

(51) Int. Cl.

| | |
|---|---|
| *E03D 9/00* | (2006.01) |
| *G01N 21/27* | (2006.01) |
| *G06T 7/00* | (2017.01) |
| *G06T 7/40* | (2017.01) |
| *G06T 7/90* | (2017.01) |

(52) U.S. Cl.

CPC .............. *E03D 9/00* (2013.01); *G06T 7/0012* (2013.01); *G06T 7/40* (2013.01); *G06T 7/90* (2017.01); *G01N 21/27* (2013.01); *G01N 2035/00306* (2013.01)

(58) Field of Classification Search

CPC ..... A61B 5/0075; A61B 5/1032; A61B 5/208; A61B 5/4875; A61B 5/6891; A61B 5/6887; E03D 9/00; G01N 2035/00306; G01N 21/27; G01N 35/00584; G01N 21/31; G06T 7/0012; G06T 7/40; G06T 7/90

See application file for complete search history.

(56) References Cited

U.S. PATENT DOCUMENTS

| | | | |
|---|---|---|---|
| 2018/0303466 A1 | 10/2018 | Kashyap et al. | |
| 2019/0195802 A1 | 6/2019 | Attar et al. | |
| 2019/0298316 A1* | 10/2019 | Kashyap | H04N 23/56 |
| 2020/0187863 A1* | 6/2020 | Tu | A47K 13/24 |
| 2020/0268303 A1* | 8/2020 | Oliva | A61B 5/202 |
| 2021/0005322 A1* | 1/2021 | Huynh | A61B 5/150022 |
| 2021/0100533 A1* | 4/2021 | Seres | A61B 5/42 |
| 2021/0389250 A1* | 12/2021 | Attar | G01J 3/10 |

FOREIGN PATENT DOCUMENTS

| | | | |
|---|---|---|---|
| JP | 2018510334 A | 4/2018 |
| JP | 2019042089 A | 3/2019 |
| KR | 20160115078 A | 10/2016 |
| KR | 20170078450 A | 7/2017 |
| WO | 2015196254 A1 | 12/2015 |
| WO | 2018222939 A1 | 12/2018 |

OTHER PUBLICATIONS

Wavelength and Color-Maple Help https://www.maplesoft.com/support/help/Maple/view.aspx?path=MathApps/WavelengthAndColor (Year: 2025).*

International Search Report and Written Opinion of the International Searching Authority in International Patent Application No. PCT/IB2021/052856, dated Apr. 6, 2021, 17 pages.

R F Kushner, D A Schoeller "Estimation of total body water by bioelectrical impedance analysis," The American Journal of Clinical Nutrition, vol. 44, Issue 3, pp. 417-424, Sep. 1986.

Weinberg AD1, Minaker KLJAMA, "Dehydration. Evaluation and management in older adults," Council on Scientific Affairs, American Medical Association. 15;274(19):1552-6, Nov. 1995.

Korean Official Action dated Dec. 20, 2024 issued in corresponding Republic of Korea application.

Joel N. Bixler et al., "Ultrasensitive detection of waste products in water using fluorescence emission cavity-enhanced spectroscopy", Proceedings of the National Academy of Sciences, May 5, 2014, vol. 111, No. 20, p. 7208-7211, DOI: 10.1073/pnas.1403175111.

Japanese Official Action dated May 20, 2025 issued in corresponding Japan application.

* cited by examiner

ANALYSIS OF BODILY EMISSONS

CROSS-REFERENCE TO RELATED APPLICATIONS

This application is a U.S. national stage of International Application No. PCT/IB2021/052856, filed on 6 Apr. 2021 and claims priority from U.S. Provisional Patent Application No. 63/006,130 to Kapp-Barnea, filed Apr. 7, 2020, entitled "Detecting and classifying dehydration," which is incorporated herein by reference.

FIELD OF EMBODIMENTS OF THE DISCLOSURE

Some applications of the present disclosure generally relate to analysis of bodily emissions. Specifically, some applications of the present disclosure relate to apparatus and methods for detecting and classifying dehydration, by analyzing bodily emissions such as urine and feces.

BACKGROUND

Dehydration is widely prevalent among older adults, and this results in significant cost to individuals and health care systems alike. Older individuals are particularly vulnerable due to a variety of reasons, including age-related changes in total body water, impaired thirst perception, renal concentrating ability, vasopressin effectiveness and medication-related hypodipsia. Functional limitations, infrequent urination, and urinary incontinence are very common amongst geriatric patients and may further increase their vulnerability to dehydration. The effects of dehydration include confusion, disorientation, nausea, dizziness, general malaise, weak spells, infection, coronary artery disease, impaired or delayed wound healing, and death. Due to the often diverse and sometimes nonspecific nature of dehydration symptoms it takes precious and critical time to diagnose it in hospital. This delay often exacerbates the condition.

Dehydration can be defined as a clinically relevant decrease of an individual's optimal Total Body Water (TBW) amount and may occur with or without loss of electrolytes. (For example, see R F Kushner, D A Schoeller "Estimation of total body water by bioelectrical impedance analysis," The American Journal of Clinical Nutrition, Volume 44, Issue 3, Pages 417-424, September 1986 and Weinberg AD1, Minaker KLJAMA, "Dehydration. Evaluation and management in older adults," Council on Scientific Affairs, American Medical Association. 15; 274(19):1552-6, November 1995.) There are at least three different forms of dehydration. Isotonic dehydration results from a balanced loss of water and sodium. For example, fasting for more than a given period of time may give rise to isotonic dehydration. Similarly, vomiting and diarrhea may give rise to isotonic dehydration because of large amounts of water and electrolytes in gastric contents. Hypertonic dehydration, which is the most common type of dehydration, results from water loss being greater than sodium loss. Characteristics of hypertonic dehydration are hypernatremia (for example, serum sodium levels of more than 145 mmol/L) and hyperosmolality (for example, serum osmolality of more than 300 mmol/kg). Fever is perhaps the most common cause of hypertonic dehydration since it often gives rise to a loss of water through the lungs and skin in combination with limited ability to increase oral fluid intake. Hypotonic dehydration occurs when sodium loss exceeds water loss. The serum sodium is decreased (for example, less than135 mmol/L) and the serum osmolality is low (for example, less than 280 mmol/kg). This type of dehydration occurs primarily with overuse of diuretics causing excess loss of sodium.

SUMMARY OF EMBODIMENTS

In accordance with some applications of the present disclosure, one or more sensors that are coupled to the toilet bowl detect one or more urine-related parameters relating to a subject's urine, without requiring any action to be performed by any person subsequent to emission of the urine into the toilet bowl. Typically, the one or more sensors that are coupled to the toilet bowl are additionally configured to detect one or more feces-related parameters relating to the subject's feces, without requiring any action to be performed by any person subsequent to emission of the feces into the toilet bowl. A computer processor receives the one or more urine-related parameters and the one or more feces-related parameters. At least partially based upon the one or more urine-related parameters, the computer processor determines that the subject is suffering from dehydration. At least partially based upon the one or more feces-related parameters, the computer processor classifies the dehydration as being a given type of dehydration, such as, isotonic dehydration, hypertonic dehydration, and hypotonic dehydration. An output may be generated, at least partially in response thereto.

For some applications, the computer processor is configured to derive a specific gravity of the subject's urine, and to determine that the subject is suffering from dehydration at least partially based upon the specific gravity of the subject's urine. For some such applications, the one or more sensors are configured to detect a signal that is indicative of absorption of cyan-green light by the subject's urine, and the computer processor is configured to derive the specific gravity of the subject's urine at least partially based upon the signal. For some applications, the sensors are configured to detect a signal that is indicative of absorption of light within a wavelength band of 480-520 nm by the subject's urine, and the computer processor is configured to derive the specific gravity of the subject's urine at least partially based upon the signal.

For some applications, the computer processor is configured to receive the one or more urine-related parameters, and to derive a parameter that is indicative of foaming and/or turbidity of the subject's urine. The computer processor estimates a concentration of albumin within the subject's urine at least partially based upon the derived parameter, and generates an output on the output device in response to the estimated concentration of albumin in the subject's urine.

For some applications, the computer processor is configured to receive the one or more urine-related parameters, and derive a concentration of at least one hemoglobin-derivative molecule within the subject's urine, at least partially based upon the urine-related parameters. Typically, the at least one hemoglobin-derivative molecule includes bilirubin, oxidized urobilinogen, and/or urobilin. The computer processor typically generates an output, at least partially in response to the derived concentration of the at least one hemoglobin-derivative molecule. For some such applications, an illumination component illuminates the subject's urine with light at a wavelength band within the range of 440-480 nm, and the sensors detect a signal that is indicative of light emitted by the subject's urine at a wavelength within a range of 505-535 nm, in response to the illumination of the subject's urine. The computer processor typically determines a concentration of oxidized urobilin within the subject's urine at least partially in response to the signal. Alternatively or additionally, the sensors are configured to detect a signal that is indicative of absorption of light within a wavelength band of 480-520 nm, by the subject's urine, and the computer processor determines a concentration of oxidized urobilino- gen within the subject's urine at least partially in response to the signal. Further alternatively or additionally, the sensors detect signals that are indicative of absorption of light by the subject's urine, within a first wavelength band of 390-420 nm and within a second wavelength band of 445-475 nm. Typically, the computer processor determines a concentra- tion of bilirubin within the subject's urine at least partially in response to the signals.

For some applications, one or more illumination compo- nents that are coupled to the toilet bowl are configured to illuminate the subject's urine with light at a wavelength band within a range of 300-520 nm. The sensors are con- figured to detect an intensity of light that is emitted by the urine at a wavelength band within a range of 530 and 560 nm in response to the illumination of the urine. The computer processor derives a level of cellulose within the subject's urine at least partially based upon the detected light inten- sity, and generates an output in response to the derived level of cellulose within the subject's urine. For some such applications, the computer processor is configured to detect that the subject is suffering from hematuria based upon a signal detected by the one or more sensors, and the computer processor is configured to drive the illumination component to illuminate the subject's urine with light at the wavelength band within the range of 300-520 nm in response to detect- ing that the subject is suffering from hematuria. Typically, the computer processor determines that a suspected cause of the subject's hematuria is biofilm-based pathogens within a urinary tract of the subject, based upon the derived level of cellulose within the subject's urine.

There is therefore provided, in accordance with some applications of the present disclosure, apparatus for use with urine and feces of a subject that are emitted into a toilet bowl and for use with an output device, the apparatus including:
    one or more sensors that are coupled to the toilet bowl, and that are configured:
        to detect one or more urine-related parameters relating to the subject's urine, without requiring any action to be performed by any person subsequent to emission of the urine into the toilet bowl, and
        to detect one or more feces-related parameters relating to the subject's feces, without requiring any action to be performed by any person subsequent to emission of the feces into the toilet bowl; and
    at least one computer processor configured to:
        receive the one or more urine-related parameters,
        receive the one or more feces-related parameters,
        at least partially based upon the one or more urine- related parameters, determine that the subject is suffering from dehydration,
        at least partially based upon the one or more feces- related parameters, classify the dehydration as being a given type of dehydration selected from the group consisting of: isotonic dehydration, hypertonic dehy- dration, and hypotonic dehydration, and
        generate an output on the output device, at least par- tially in response thereto.
In some applications, the at least one computer processor is configured to detect the one or more urine-related param- eters relating to the subject's urine by detecting urine color. In some applications, the at least one computer processor is configured to detect the one or more urine-related parameters relating to the subject's urine by detecting urine volume. In some applications, the at least one computer processor is configured to detect the one or more urine- related parameters relating to the subject's urine by detect- ing urine voiding duration.

In some applications, the at least one computer processor is configured to detect the one or more feces-related param- eters relating to the subject's feces by detecting one or more feces-related parameters selected from the group consisting of: shape, size texture, and color.

In some applications, the at least one computer processor is configured to detect the one or more urine-related param- eters relating to the subject's urine by detecting urine voiding frequency of the subject. In some applications, the at least one computer processor is configured to detect urine voiding frequency of the subject by automatically detecting which person is urinating at a given time.

In some applications, the at least one computer processor is configured to detect the one or more feces-related param- eters relating to the subject's feces by performing computer- vision analysis on an image of the feces. In some applica- tions, the at least one computer processor is configured to perform computer-vision analysis on the image of the feces by performing one or more steps selected from the group consisting of: masking, contrast enhancement, image-edge detection, region-of-interest detection, applying morpho- logical changes, and performing segmentation.

In some applications, the at least one computer processor is configured to derive a specific gravity of the subject's urine, and to determine that the subject is suffering from dehydration at least partially based upon the specific gravity of the subject's urine. In some applications, the one or more sensors are configured to detect a signal that is indicative of absorption of cyan-green light by the subject's urine, and the at least one computer processor is configured to derive the specific gravity of the subject's urine at least partially based upon the signal. In some applications, the one or more sensors are configured to detect a signal that is indicative of absorption of light within a wavelength band of 480-520 nm by the subject's urine, and the at least one computer pro- cessor is configured to derive the specific gravity of the subject's urine at least partially based upon the signal.

There is further provided, in accordance with some appli- cations of the present disclosure, a method for use with urine and feces of a subject that are emitted into a toilet bowl, the method including:
    using one or more sensors that are coupled to the toilet bowl, detecting one or more urine-related parameters relating to the subject's urine, without requiring any action to be performed by any person subsequent to emission of the urine into the toilet bowl;
    using the one or more sensors that are coupled to the toilet bowl, detecting one or more feces-related parameters relating to the subject's feces, without requiring any action to be performed by any person subsequent to emission of the feces into the toilet bowl; and
    using a computer processor:
        receiving the one or more urine-related parameters;
        receiving the one or more feces-related parameters;
        at least partially based upon the one or more urine- related parameters, determining that the subject is suffering from dehydration;
        at least partially based upon the one or more feces- related parameters, classifying the dehydration as being a given type of dehydration selected from the group consisting of: isotonic dehydration, hypertonic dehydration, and hypotonic dehydration; and generating an output on an output device, at least partially in response thereto.

In some applications, detecting one or more urine-related parameters relating to the subject's urine includes detecting urine color. In some applications, detecting one or more urine-related parameters relating to the subject's urine includes detecting urine volume. In some applications, detecting urine volume includes detecting urine voiding duration.

In some applications, detecting one or more feces-related parameters relating to the subject's feces includes detecting one or more feces-related parameters selected from the group consisting of: shape, size texture, and color.

In some applications, detecting one or more urine-related parameters relating to the subject's urine includes detecting urine voiding frequency of the subject. In some applications, detecting urine voiding frequency of the subject includes automatically detecting which person is urinating at a given time.

In some applications, detecting one or more feces-related parameters relating to the subject's feces includes performing computer-vision analysis on an image of the feces. In some applications, performing computer-vision analysis on the image of the feces includes performing one or more steps selected from the group consisting of: masking, contrast enhancement, image-edge detection, region-of-interest detection, applying morphological changes, and performing segmentation.

In some applications, determining that the subject is suffering from dehydration includes deriving a specific gravity of the subject's urine, and determining that the subject is suffering from dehydration at least partially based upon the specific gravity of the subject's urine. In some applications, deriving specific gravity of the subject's urine includes detecting a signal that is indicative of absorption of cyan-green light by the subject's urine, and deriving the specific gravity of the subject's urine at least partially based upon the signal. In some applications, deriving specific gravity of the subject's urine includes detecting a signal that is indicative of absorption of light within a wavelength band of 480-520 nm by the subject's urine, and deriving the specific gravity of the subject's urine at least partially based upon the signal.

There is further provided, in accordance with some applications of the present disclosure, apparatus for use with urine of a subject that is emitted into a toilet bowl and for use with an output device, the apparatus including:

one or more sensors that are coupled to the toilet bowl, and that are configured to detect one or more urine-related parameters relating to the subject's urine, without requiring any action to be performed by any person subsequent to emission of the urine into the toilet bowl, and at least one computer processor configured to:

receive the one or more urine-related parameters, and derive a concentration of at least one hemoglobin-derivative molecule within the subject's urine, at least partially based upon the urine-related parameters, the at least one hemoglobin-derivative molecule being selected from the group consisting of: bilirubin, oxidized urobilinogen, and urobilin, and generate an output on the output device, at least partially in response to the derived concentration of the at least one hemoglobin-derivative molecule.

In some applications, the apparatus further includes an illumination component configured to illuminate the subject's urine with light at a wavelength band within the range of 440-480 nm, the one or more sensors are configured to detect a signal that is indicative of light emitted by the subject's urine at a wavelength within a range of 505-535 nm, in response to the illumination of the subject's urine, and the at least one computer processor is configured to determine a concentration of oxidized urobilin within the subject's urine at least partially in response to the signal.

In some applications, the one or more sensors are configured to detect a signal that is indicative of absorption of light within a wavelength band of 480-520 nm, by the subject's urine, and the at least one computer processor is configured to determine a concentration of oxidized urobilinogen within the subject's urine at least partially in response to the signal.

In some applications, the one or more sensors are configured to detect signals that are indicative of absorption of light by the subject's urine, within a first wavelength band of 390-420 nm and within a second wavelength band of 445-475 nm, and the at least one computer processor is configured to determine a concentration of bilirubin within the subject's urine at least partially in response to the signals. In some applications, the at least one computer processor is configured to determine a ratio of light absorption by the subject's urine at each of the first and second wavelength bands with respect to each other, and to determine concentration of bilirubin within the subject's urine based upon the ratio.

There is further provided, in accordance with some applications of the present disclosure, apparatus for use with urine of a subject that is emitted into a toilet bowl and for use with an output device, the apparatus including:

one or more sensors that are coupled to the toilet bowl, and that are configured to detect one or more urine-related parameters relating to the subject's urine, without requiring any action to be performed by any person subsequent to emission of the urine into the toilet bowl, and at least one computer processor configured to:

receive the one or more urine-related parameters, and derive a parameter that is indicative of foaming and/or turbidity of the subject's urine, estimate a concentration of albumin within the subject's urine at least partially based upon the derived parameter, and in response to the estimated concentration of albumin in the subject's urine, generate an output on the output device.

There is further provided, in accordance with some applications of the present disclosure, apparatus for use with urine of a subject that is emitted into a toilet bowl and for use with an output device, the apparatus including:

one or more illumination components that are coupled to the toilet bowl and that are configured to illuminate the subject's urine with light at a wavelength band within a range of 300-520 nm;

one or more sensors that are coupled to the toilet bowl, and that are configured to detect an intensity of light that is emitted by the urine at a wavelength band within a range of 530 and 560 nm in response to the illumination of the urine; and at least one computer processor configured to:

derive a level of cellulose within the subject's urine at least partially based upon the detected light intensity, and generate an output on the output device in response to the derived level of cellulose within the subject's urine.

In some applications, the computer processor is configured to detect that the subject is suffering from hematuria based upon a signal detected by the one or more sensors, and the computer processor is configured to drive the illumination component to illuminate the subject's urine with light at the wavelength band within the range of 300-520 nm in response to detecting that the subject is suffering from hematuria. In some applications, the computer processor is configured to determine that a suspected cause of the subject's hematuria is biofilm-based pathogens within a urinary tract of the subject based upon the derived level of cellulose within the subject's urine.

The present disclosure will be more fully understood from the following detailed description of embodiments thereof, taken together with the drawings, in which:

DETAILED DESCRIPTION OF EMBODIMENTS

Figure 1:
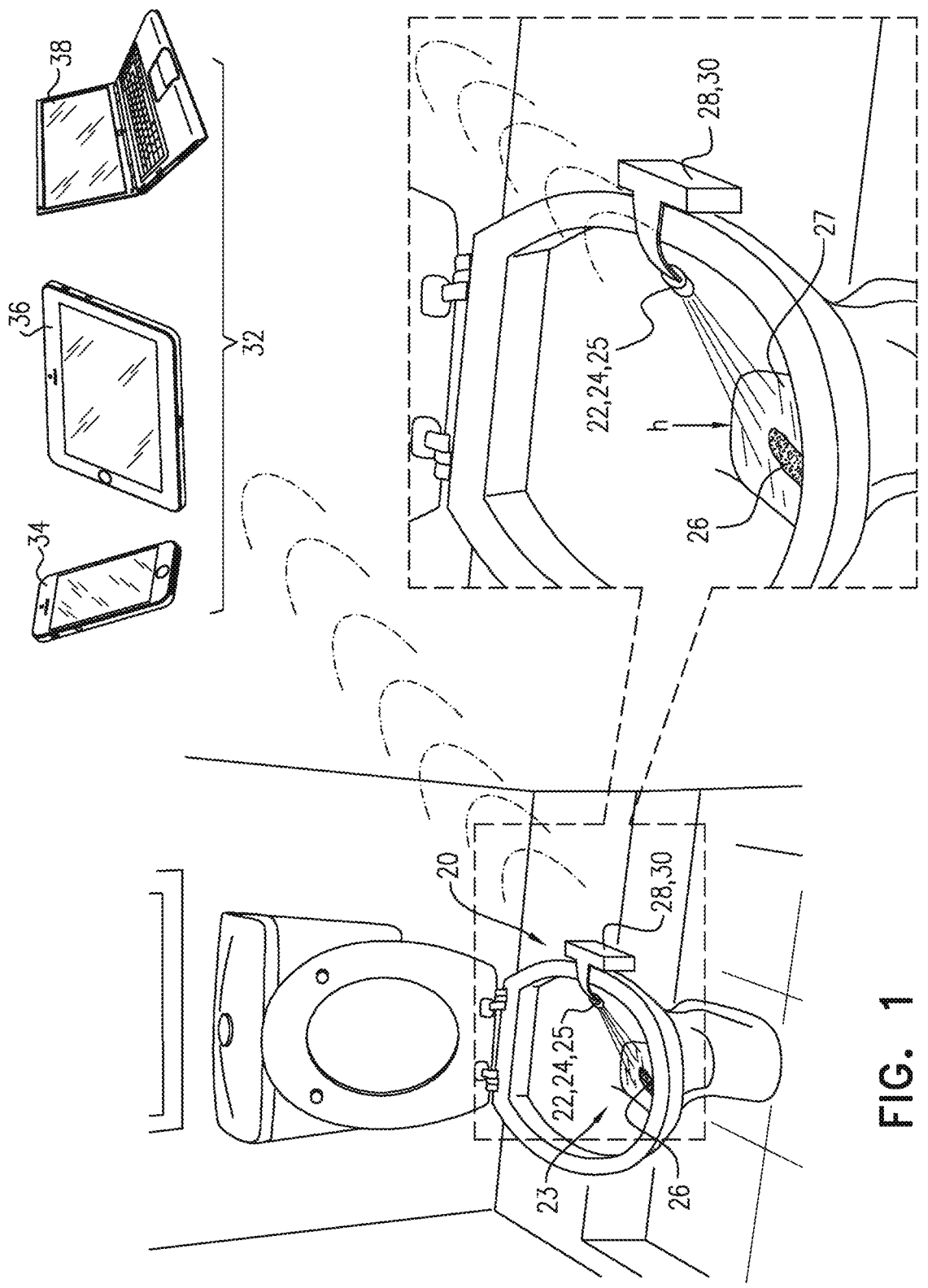
FIG. 1 is a schematic illustration of apparatus for analyzing a bodily emission, in accordance with some applications of the present disclosure.

Reference is now made to FIG. 1, which is a schematic illustration of apparatus 20 for analyzing bodily emissions, in accordance with some applications of the present disclosure. As shown, apparatus 20 typically includes a sensor module 22, which is placed inside a toilet bowl 23. For some applications, the sensor module (and/or additional components of the apparatus) is integrated into the toilet bowl. The sensor module includes one or more sensors 24. Typically, the one or more sensors are configured to detect one or more urine-related parameters (such as, voiding frequency, urine volume, urine color, and/or urine concentration, etc.), and to detect one or more feces-related parameters (such as, feces shape, size, texture, etc.). For some applications, the one or more sensors detect at least some of the aforementioned parameters while the bodily emission is being emitted by the subject into the toilet bowl. Alternatively or additionally, the one or more sensors detect at least some of the aforementioned parameters when the bodily emission is disposed within the toilet bowl, subsequent to its emission by the subject. For some applications, the sensors include an imaging component, such as an RGB camera, a spectral camera, and/or a hyperspectral camera. Alternatively or additionally, the one or more sensors may include one or more light sensors that are configured to receive light from the bodily emissions. For some applications, the sensor module includes one or more illumination components 25. In accordance with respective applications, such illumination components include illumination components that are configured to illuminate the bodily emissions at given spectral bands (e.g., LEDs and/or lasers), and/or a broadband light source. For some applications, a broadband light source is used in combination with one or more bandpass filters (which may be used to filter the emitted and/or the detected light).

A computer processor typically receives the one or more urine-related parameters from the one or more sensors, as well as receiving the one or more feces-related parameters from the one or more sensors. In accordance with respective applications, the computer processor that performs the analysis described herein is a computer processor 28 disposed inside housing 30 (which typically also houses the sensor module), or is a different computer processor that is in communication with the sensor module. Typically, at least partially based upon the one or more urine-related parameters, the computer processor determines that the subject is suffering from dehydration. For example, the one or more urine-related parameters that are detected by the one or more sensors may include urine color, urine volume (which may be measured by detecting a height h of the urine within the toilet bowl), voiding duration (which may be measured by detecting the period of time over which the height h of the urine within the toilet bowl rises), and/or voiding frequency. Typically, in order to detect voiding frequency of a particular subject, the sensor module is configured to receive an input from the subject to indicate that they are currently using the toilet, or the sensor module is configured to automatically detect which subject is urinating into the toilet bowl at a given time.

For some applications, at least partially based upon the one or more feces-related parameters (such as, feces shape, size, texture, color etc.), the computer processor classifies the dehydration as being a given type of dehydration, such as, isotonic dehydration, hypertonic dehydration, or hypotonic dehydration. For example, the one or more sensors may include one or more cameras. For such applications, the computer processor typically receives one or more images of the feces, and analyzes the images to determine spatial, and/or textural, and/or color parameters of the feces. For some applications, images captured at a plurality of different wavelengths are analyzed. For example, the feces may be illuminated with light at plurality of different wavelengths at respective times and images may be acquired while the feces are illuminated under respective illumination wavelengths. Alternatively or additionally, the images may be acquired using filters, cameras, and/or other imaging devices or light detection devices (such as a spectrometer, a spectral camera, a hyperspectral camera, etc.) that are configured to acquire images at different wavelengths. For some applications, the analysis of the images of the feces is performed using a computer-vision analysis algorithm that performs segmentation and/or texture classification. Alternatively or additionally, the image analysis is performed using a deep neural network trained for this task.

By way of illustration and not limitation, some representative examples of steps that the computer-vision analysis algorithm may include are as follows:

masking, e.g., to exclude peripheral areas that are remote from the feces;

contrast enhancement to enhance the region of the image in which the feces are disposed;

image-edge detection to detect the edge of the feces;

detecting a region-of-interest, e.g., using a Gaussian Mixture Model;

performing morphological changes for noise cleaning; performing segmentation using GrabCut.

Reference is made to FIGS. 2A, 2B, 2C, 2D, and 2E, which show representative images of the some of the above-described computer-vision analysis steps being performed upon an image of feces in a toilet bowl, in accordance with some applications of the present disclosure.

Figure 2A:
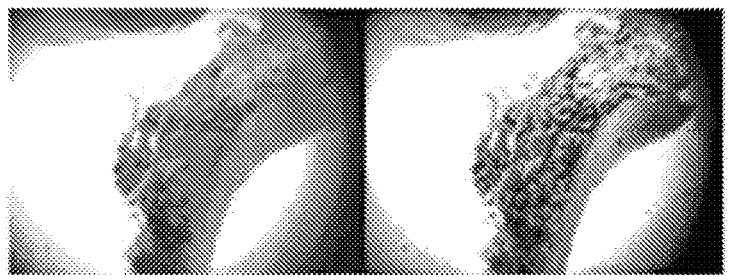
FIGS. 2A, 2B, 2C, 2D, and 2E show representative images of the some computer-vision analysis steps that are performed upon an image of feces in a toilet bowl, in accordance with some applications of the present disclosure.

FIG. 2A is an example of contrast enhancement being performed on an image of a subject's feces, with the left frame showing the image of the feces prior to being enhanced and the right frame showing the enhanced image.

Figure 2B:
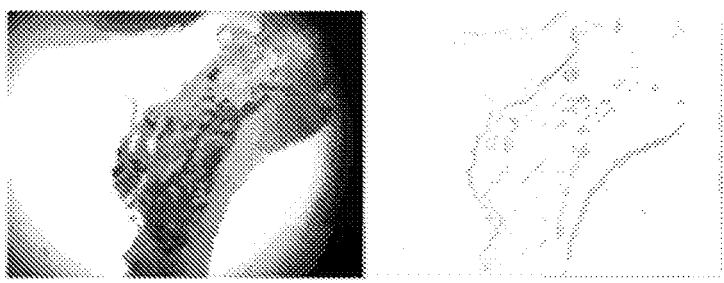

FIG. 2B is an example of edge detection being performed on an image of subject's feces, with the left frame showing the image of the feces prior to the edge detection algorithm being applied and the right frame showing the output of the edge detection algorithm.

Figure 2C:
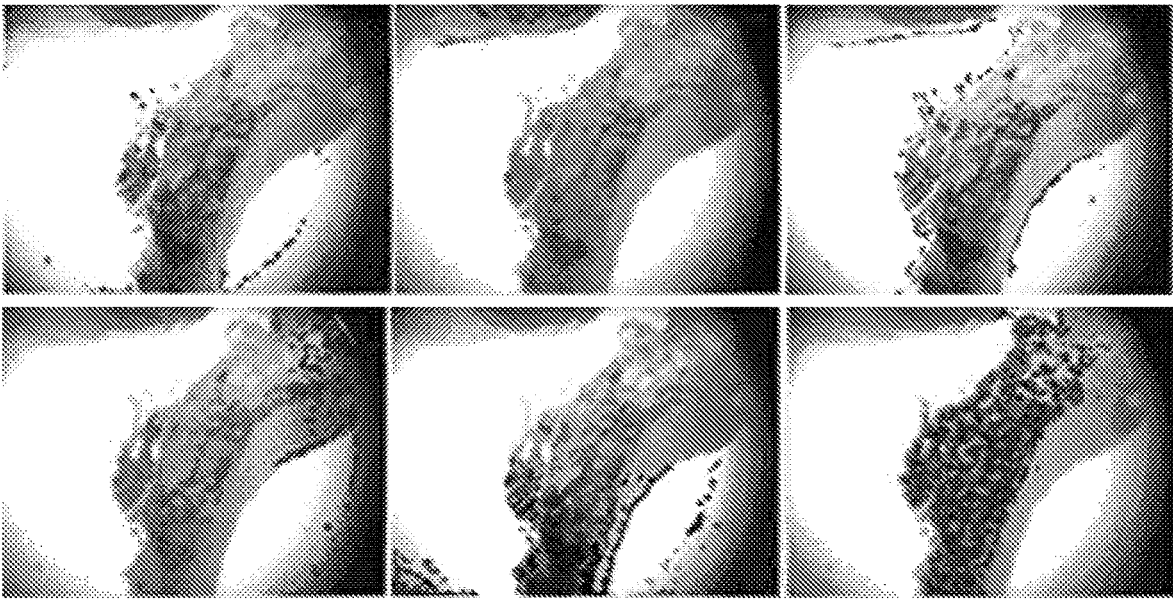

FIG. 2C is an example of the detection of a region of interest being performed on an image of subject's feces using a Gaussian mixture model. The sequence of images shows respective clusters that are identified as being regions of interest within the image. Each of the regions of interest is typically then subjected to further analysis in order to detect parameters relating to the subject's feces.

Figure 2D:
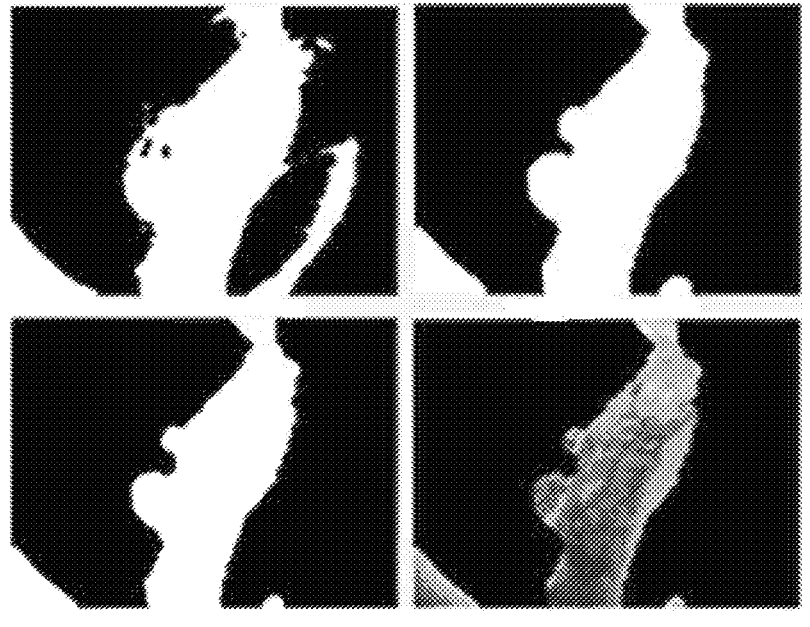

FIG. 2D shows respective stages of a noise-cleaning algorithm being applied to an image of a subject's feces, whereby morphological changes are applied to the image in order to clean noise from the image.

Figure 2E:
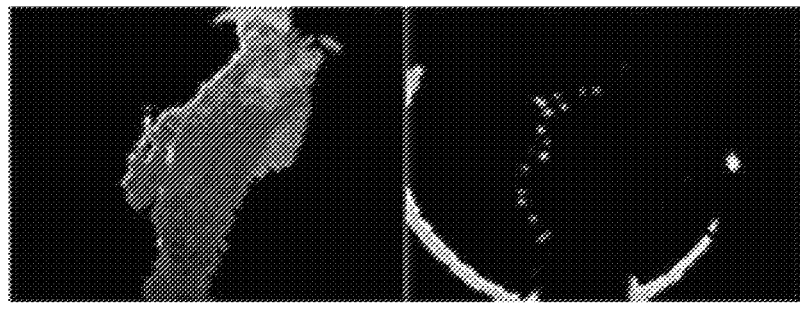

FIG. 2E is an example of GrabCut image segmentation algorithm being applied to an image of a subject's feces, with the left frame showing the image of the feces prior to the GrabCut image segmentation algorithm being applied and the right frame showing the output of the GrabCut image segmentation algorithm.

Typically, computer processor 28 generates an output on an output device (e.g., a user interface device 32, described hereinbelow), based upon the detection and classification of the dehydration. For example, the computer processor may generate an output indicating that the subject is suffering from a given type of dehydration, and/or may generate an output indicating a recommended course of action for the subject based on the type of dehydration. In this regard it is noted that different courses of action are typically recommended for patients suffering from dehydration, depending on the type of dehydration.

It is noted that although FIG. 1 shows urine 27 and feces 26 of the subject disposed in the toilet bowl at the same time as each other, the scope of the present application includes analyzing feces of the subject at a separate time from analyzing urine of the subject. For example, it may first be determined that the subject is suffering from dehydration, by analyzing the subject's urine. Subsequently, upon the subject defecating, the subject's feces may be analyzed in order to classify the subject's dehydration as a given type of dehydration, as described hereinabove.

For some applications, the apparatus and methods described herein are performed in conjunction with apparatus and methods described in U.S. Pat. No. 10,575,830 to Attar and/or in US 2019/0195802 to Attar, both of which applications are which is incorporated herein by reference.

For some applications, apparatus 20 includes a power source (e.g., a battery pack), that is disposed outside the toilet bowl inside housing 30. Alternatively or additionally, the sensor module is connected to mains electricity. Typically, the power source and sensor module 22 are connected wiredly (as shown), or wirelessly. In accordance with respective applications, the computer processor that performs the above described analysis is disposed inside the toilet bowl (e.g., computer processor 28 disposed inside housing 30 (which typically also houses the sensor module)), or remotely. For example, as shown, the sensor module may communicate wirelessly with a user interface device 32 that includes a computer processor. Such a user interface device may include, but is not limited to, a phone 34, a tablet computer 36, a laptop computer 38, or a different sort of personal computing device. The user interface device typically acts as both an input device and an output device, via which the user interacts with sensor module 22. The sensor module may transmit data to the user interface device and the user interface device computer processor may run a program that is configured to analyze the received data.

For some applications, sensor module 22 and/or the user interface device communicates with a remote server. For example, the apparatus may communicate with a physician or an insurance company over a communication network without intervention from the subject. The physician or the insurance company may evaluate the results and determine whether further testing or intervention is appropriate for the subject. For some applications, data relating to the received sensor signals are stored in a memory. For example, the memory may be disposed inside the toilet bowl (e.g., inside the sensor unit), inside housing 30, or remotely. Periodically, the subject may submit the stored data to a facility, such as a healthcare facility (e.g., a physician's office, or a pharmacy) or an insurance company, and a computer processor at the facility may then perform the above-described analysis on a batch of data relating to a plurality of bodily emissions of the subject that were acquired over a period of time.

It is noted that the apparatus and methods described herein include a screening test in which the subject is not required to physically touch the bodily emission. Furthermore, the subject is typically only required to touch any portion of the dedicated sensing apparatus periodically, for example, in order to install the device, or to change or recharge the device batteries. (It is noted that the subject may handle the user interface device, but this is typically a device (such as a phone) that subject handles even when not using the sensing apparatus.) Further typically, the apparatus and methods described herein do not require adding anything to the toilet bowl subsequent to the subject emitting a bodily emission into the toilet bowl, in order to facilitate the analysis of the emission, and/or a determination that the subject is suffering from dehydration and the classification thereof. For some applications, the subject is not required to perform any action after installation of the apparatus in the toilet bowl. The testing is automatic and handled by the apparatus, and monitoring of the subject's emissions is seamless to the subject and does not require compliance by the subject, so long as no abnormality is detected.

Typically, subsequent to the subject emitting a bodily emission into the toilet bowl (and typically once the subject has finished excreting the bodily emission, and the bodily emission is at least partially disposed within the water of the toilet bowl), the bodily emission is imaged by receiving reflected and/or transmitted light from the toilet bowl, without requiring any action to be performed by any person subsequent to the emission. For some applications, the bodily emission is analyzed during the emission of the bodily emission into the toilet bowl.

For some applications, for each emission of the subject, in the case of positive signal, the apparatus reports the finding to the subject via an output device, e.g., via user interface device 32. For some applications, the output device includes an output component (such as a light (e.g., an LED) or a screen) that is built into apparatus 20.

Sensor module 22 is typically disposed inside a toilet bowl. Further typically, the sensor module includes an imaging component, which in turn includes one or more light sensors that are configured to receive light from bodily emissions that were emitted by the subject and are disposed inside the toilet bowl. Typically, the sensor module is housed in a water-resistant housing. Further typically, the face of the sensor module underneath which the imaging component is mounted is covered with a transparent, water-resistant cover. It is noted that FIG. 1 shows the sensor module disposed above the water level of the water within the toilet bowl. However, for some applications, at least a portion of the sensor module (e.g., the entire sensor module) is submerged within the water in the toilet bowl.

For some applications, the sensor module includes a subject sensor. The subject sensor is configured to detect when a subject is on or in the vicinity of the toilet, and/or if the subject has defecated and/or urinated into the toilet bowl. For example, the subject sensor may include a motion sensor, configured to sense the motion of feces, urine, the subject, or the water in the toilet bowl. Alternatively or additionally, the subject sensor may include a light sensor configured to detect when the light in the bathroom is switched on, or when the subject sits on the toilet. For some applications, light sensors that are used for detecting light from the bodily emission are also used for the aforementioned function. For some such applications, the sensor module is configured to be in standby mode most of the time (such that the sensor module uses a reduced amount of power). The sensor module is switched on in response to detecting that the subject is on or in the vicinity of the toilet, and/or that the subject has defecated and/or urinated into the toilet bowl. Typically, the imaging component of the sensor module acquires images in response to detecting that the subject is on or in the vicinity of the toilet, and/or that the subject has defecated and/or urinated into the toilet bowl. For some applications, the subject switches on the sensor module manually.

For some applications, the computer processor 28 is configured to detect one or more additional components and/or parameters of the subject's urine, based upon data acquired by sensor module 22. Some such application are described hereinbelow.

Urinary Specific Gravity

Urinary specific gravity is a measure of the concentration of solutes in the urine. Urinary specific gravity measures the ratio of urine density compared with water density and provides information on the kidney's ability to concentrate urine. Typically, healthy adult urine has a specific gravity in the range of 1.010 to 1.030. Increased specific gravity (known as hypersthenuria) may be associated with dehydration, diarrhea, emesis, excessive sweating, urinary tract/bladder infection, glucosuria, renal artery stenosis, hepatorenal syndrome, decreased blood flow to the kidney (especially as a result of heart failure), and/or an excess of antidiuretic hormone. Decreased specific gravity (also known as hyposthenuria) may be associated with renal failure, pyelonephritis, diabetes insipidus, acute tubular necrosis, interstitial nephritis, and excessive fluid intake (e.g., psychogenic polydipsia).

For some applications, the sensor module is configured to generate a signal that is indicative of the absorption of light by the subject's urine, and the computer processor derives the specific gravity of the subject's urine based upon the signal. Typically, the computer processor derives the specific gravity of the subject's urine based upon a sensor signal that is indicative of the absorption of cyan-green light (e.g., light within a wavelength band of 480-520 nm), by the subject's urine. For some applications, the computer processor generates an output in response to the derived specific gravity. For example, the computer processor may generate an output on user interface device 32 indicating that the subject is suffering from dehydration, and/or may generate an output on user interface device 32 indicating a recommended course of action for the subject. For some applications, the computer processor is configured to detect that the subject is suffering from dehydration based upon the specific gravity of the subject's urine, and is configured to categorize the dehydration using the techniques described hereinabove.

Figure 3:
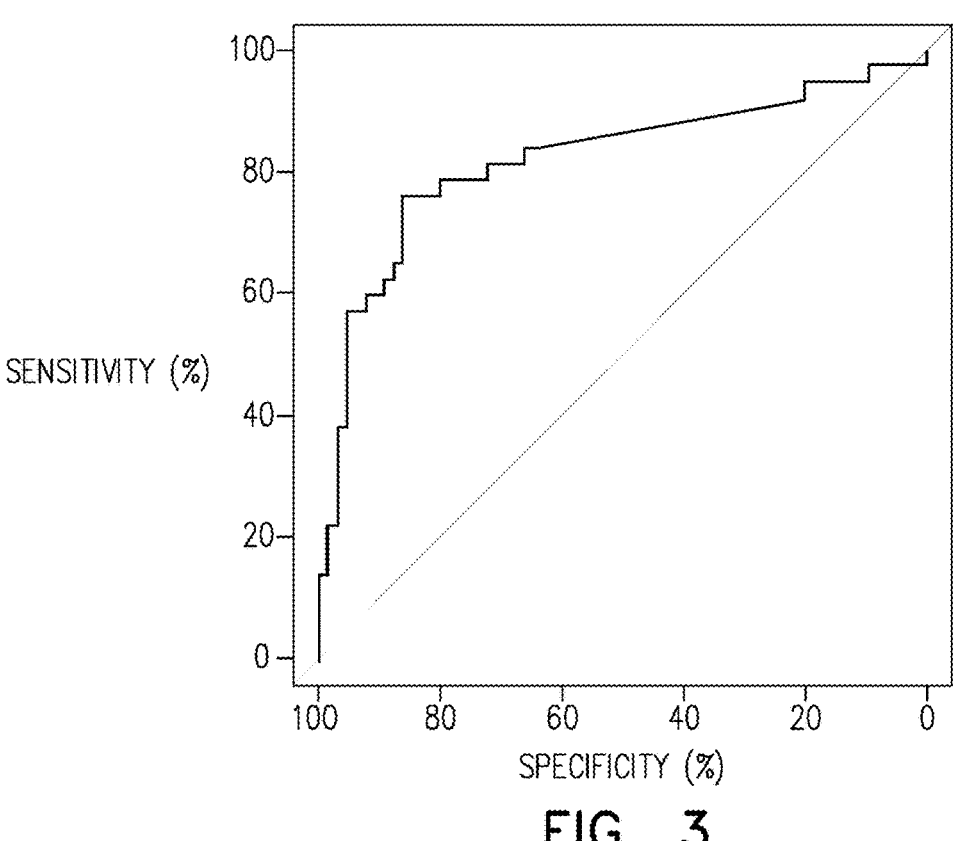
FIG. 3 is a receiver operating characteristic (ROC) curve showing the sensitivity and specificity of a classifier for detecting specific gravity of urine that is based upon blue-light absorption by the urine, in accordance with some applications of the present disclosure.

Reference is now made to FIG. 3, which is an ROC curve showing the sensitivity and specificity of a classifier for detecting specific gravity of urine that is based upon blue-light absorption by the urine, in accordance with some applications of the present disclosure. The results shown in FIG. 3 are for a classifier for which a specific gravity of 1.025 was used as the classification point (i.e., specific gravity of less than 1.025 was deemed to be indicative of either isosthenuria or hyposthenuria, and specific gravity of more than 1.025 was deemed to be indicative of hypersthenuria). The results of the classifier were compared to results as obtained using Multistix® 10 SG reagent strips, manufactured by Siemens (Germany). The classifier yielded a sensitivity of 81 percent and specificity of 80.0 percent with an area under curve ("AUC") of 82 percent, indicating that the classifier is a reliable classifier for determining specific gravity.

Hematuria

Blood in human urine (known as hematuria) is a warning sign of various serious conditions of the urinary tract, some of which can be life-threatening. For example, hematuria might result from a urinary tract infection, kidney infections, bladder or kidney stones, an enlarged prostate, kidney disease, viral or strep infections, or cancers of the bladder and kidneys. For some applications, the computer processor analyzes the signal from the sensor module to determine that the subject is suffering from hematuria. For some such applications, the computer processor uses techniques as described in U.S. Pat. No. 10,575,830 to Attar, which is incorporated herein by reference.

Figure 4:
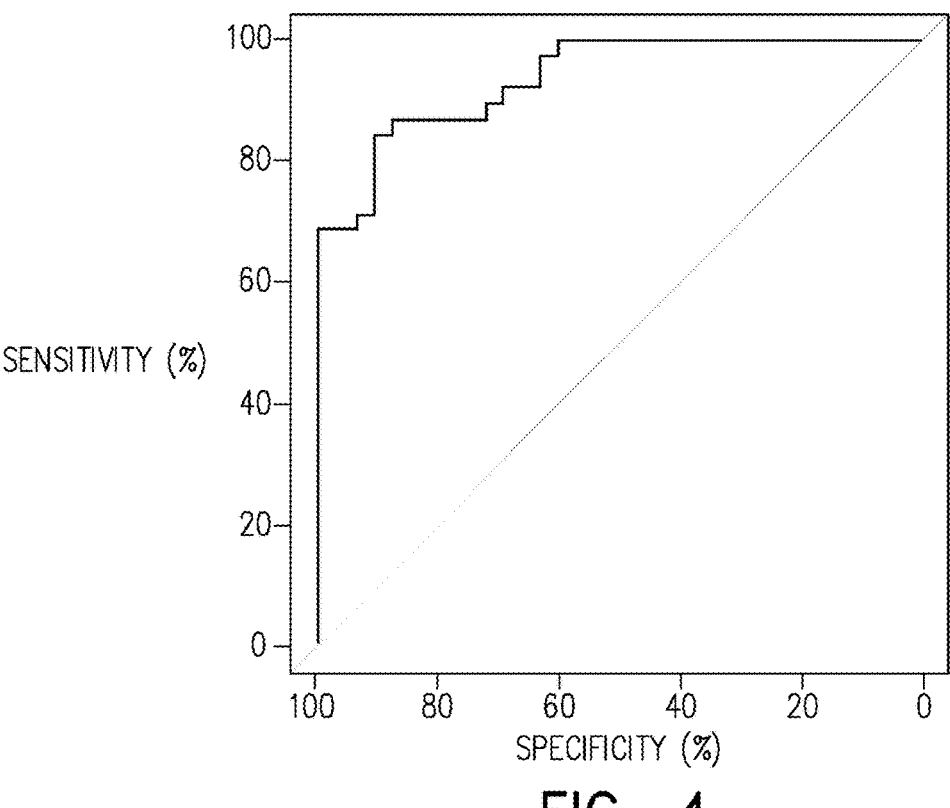
FIG. 4 is an ROC curve showing the sensitivity and specificity of a classifier that utilized a sensor module as described herein to detect the presence of blood in subjects' urine, in accordance with some applications of the present disclosure.

Reference is now made to FIG. 4, which is an ROC curve showing the sensitivity and specificity of a classifier that utilized a sensor module as described herein to detect the presence of blood in subjects' urine, in accordance with some applications of the present disclosure. The classifier yielded a sensitivity of 80.5 percent and 80.8 percent specificity with an AUC of more than 88 percent, when compared with the results of a hemoglobin immunoassay performed with a QuikRead go wrCRP+Hb instrument, manufactured by Aidian (Espoo, Finland), indicating that a sensor as described herein may be used to reliably detect the presence of blood in a subject's urine.

Bilirubin, Oxidized Urobilinogen, and Urobilin

Bilirubin, urobilin, and urobilinogen are all derivative molecules of Hemoglobin metabolism in the liver. Urobilinogen is a colorless by-product of bilirubin reduction. In liver disease (such as hepatitis), urobilinogen levels are increased. When urobilinogen is exposed to air, it is oxidized to urobilin, which gives urine its yellow color.

Bilirubin has a distinct absorption spectrum, exhibiting a trough in its absorption spectrum at a wavelength band within the range of 390-420 nm (e.g., approximately 400-

410 nm), and (b) a peak within the range of 445-475 nm (e.g., approximately 455-465 nm). Therefore, for some applications of the present disclosure, the sensor module is configured to detect light absorption at each of the aforementioned wavelength bands, and the computer processor is configured to determine a concentration of bilirubin in the subject's urine in response thereto. For some such applications, the computer processor determines the ratio of light absorption at each of the aforementioned wavelength bands with respect to each other, and determines a concentration of bilirubin in the subject's urine based upon the ratio. For some applications, the computer processor is configured to generate an output in response to the detected bilirubin concentration. For example, in response to a high concentration of bilirubin, the computer processor may generate an output on the user interface device indicating that the subject should seek medical attention.

Oxidized urobilinogen has a distinct absorption spectrum, exhibiting a peak in its absorption spectrum at a wavelength band within the range of 480-520 nm, e.g., approximately 500-515 nm. Therefore, for some applications of the present disclosure, the sensor module is configured to detect light absorption at the aforementioned wavelength band, and the computer processor is configured to determine a concentration of oxidized urobilinogen in the subject's urine in response thereto. For some applications, the computer processor is configured to generate an output in response to the detected oxidized urobilinogen concentration. For example, in response to a high concentration of oxidized urobilinogen, the computer processor may generate an output on the user interface device indicating that the subject should seek medical attention.

It has additionally been demonstrated that pre-illumination of urobilin at a wavelength of approximately 460 nm (e.g., between 440 nm and 480 nm) causes the urobilin to emit light (due to autofluorescence) at a wavelength of approximately 520 nm. Therefore, in accordance with some applications of the present disclosure, the subject's urine is illuminated with illumination at a wavelength band within the range of 440-480 nm (e.g., using illumination components 25, shown in FIG. 1). The computer processor then analyzes the sensor signal to determine the intensity of light that is emitted by the urine at a wavelength of approximately 520 nm (e.g., at a wavelength band within the range of 505-535 nm, or a wavelength band within the range of 515-525 nm), in response to the illumination of the urine. Typically, the computer processor is configured to determine a concentration of oxidized urobilin in the subject's urine in response thereto.

Protein (e.g., Albumin)

Protein (e.g., albumin) is normally abundant in the blood. If there is a problem with kidneys, protein can leak into urine. A large amount of protein in urine may indicate kidney disease. Although protein in urine tends not to have an optical signature, it has been observed that the presence of protein within a subject's urine can give rise to foaming of the urine because the protein has a soap-like effect that decreases the surface tension of urine. Expulsion of urine causes interaction of the electrostatic forces between molecules within the liquid and surface, leading to the formation of bubbles as a result of dispersion of air in the urine. For some applications, the computer processor is configured to detect a sensor signal that is indicative of foaming and/or turbidity of the subject's urine, and/or an amount of foaming and/or turbidity of the urine, and is configured to determine that the subject has an excess of protein in her/his urine at least partially in response thereto. Alternatively or additionally, the computer processor is configured to estimate a concentration of protein in the subject's urine, in response to foaming and/or turbidity of the subject's urine, and/or an amount of foaming and/or turbidity of the urine. For some such applications, the computer processor is configured to estimate turbidity of the urine by detecting opacity of the urine. For some applications, the computer processor is configured to measure a height of a foam layer above the urine, and to determine that the subject has an excess of protein in her/his urine, and/or estimate a concentration of protein in the subject's urine, in response thereto. For some applications, the computer processor is configured to generate an output in response to detecting an excess of protein in the subject's urine, and/or based upon the estimated concentration of protein in the subject's urine. For example, in response to detecting an excess of protein in the subject's urine, and/or based upon the estimated concentration of protein in the subject's urine, the computer processor may generate an output on the user interface device indicating that the subject should seek medical attention.

Biofilm-Based Pathogens

It has been suggested that a cause of recurrent urinary tract infections (UTIs) is the formation of pathogens (such as UroPathogenic *Escherichia coli* (UPEC)) into a biofilm within the urinary tract Typically, in such cases, cellulose is present within a biofilm extracellular matrix within the urinary tract. It has additionally been demonstrated that pre-illumination of cellulose with wideband illumination at a wavelength band within the range of 300-520 nm causes the cellulose to emit light (due to autofluorescence) at a wavelength of approximately 545 nm. Therefore, in accordance with some applications of the present disclosure, the subject's urine is illuminated with wideband illumination at a wavelength band within the range of 300-520 nm (e.g., using illumination components 25, shown in FIG. 1). The computer processor then analyzes the sensor signal to determine the intensity of light that is emitted by the urine at a wavelength of approximately 545 nm (e.g., at a wavelength band within a range of 530 and 560 nm, or a wavelength band within a range of 540-550 nm), in response to the illumination of the urine.

For some applications, the computer processor is configured to derive a level of cellulose within the subject's urine at least partially based upon the detected light intensity. As described hereinabove, for some applications, the computer processor is configured to detect hematuria by analyzing the sensor signal. For some applications, in response to detecting hematuria (e.g., using the above-described techniques), the computer processor is configured to (a) drive the illumination components 25 to illuminate the subject's urine with wideband illumination at a wavelength band within the range of 300-520 nm and (b) determine the intensity of light that is emitted by the urine at a wavelength of approximately 545 nm (e.g., at a wavelength of between 530 and 560 nm, or a wavelength of 540-550 nm), in response to the illumination of the urine. Based upon the detected light intensity (and the derived concentration of cellulose within the urine) the computer processor is configured to perform a differential diagnosis and to determine whether the suspected cause of the hematuria is of biofilm-based pathogens within the subject's urinary tract. For some such applications, the computer processor generate an output in response to the differential diagnosis. For example, the computer processor may generate an output on the user interface device 32 indicating that the subject should seek medical attention.

Applications of the disclosure described herein can take the form of a computer program product accessible from a computer-usable or computer-readable medium (e.g., a non-transitory computer-readable medium) providing program code for use by or in connection with a computer or any instruction execution system, such as a computer processor of user interface device 32, computer processor 28 disposed within housing 30, or a remote cloud-based computer processor. For the purpose of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer-usable or computer readable medium is a non-transitory computer-usable or computer readable medium.

Examples of a computer-readable medium include a semiconductor or solid-state memory, magnetic tape, a removable computer diskette, a random-access memory (RAM), a read-only memory (ROM), a rigid magnetic disk and an optical disk. Current examples of optical disks include compact disk-read only memory (CD-ROM), compact disk-read/write (CD-R/W) and DVD. For some applications, cloud storage is used.

A data processing system suitable for storing and/or executing program code will include at least one processor (e.g., a computer processor of user interface device 32, computer processor 28 disposed within housing 30, or a remote cloud-based computer processor) coupled directly or indirectly to memory elements (e.g., a memory of user interface device 32) through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the disclosure.

Network adapters may be coupled to the processor to enable the processor to become coupled to other processors or remote printers or storage devices through intervening private or public networks. Modems, cable modem and Ethernet cards are just a few of the currently available types of network adapters.

Computer program code for carrying out operations of the present disclosure may be written in any combination of one or more programming languages, including an object-oriented programming language such as Java, Smalltalk, C++ or the like and conventional procedural programming languages, such as the C programming language or similar programming languages.

It will be understood that the algorithms described herein can be implemented by computer program instructions. These computer program instructions may be provided to a processor of a general purpose computer, special purpose computer, or other programmable data processing apparatus to produce a machine, such that the instructions, which execute via the processor of the computer (e.g., a computer processor of user interface device 32, computer processor 28 disposed within housing 30, or a remote cloud-based computer processor) or other programmable data processing apparatus, create means for implementing the functions/acts specified in the algorithms described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the algorithms The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the algorithms described in the present application.

The computer processors described herein are typically hardware devices programmed with computer program instructions to produce a special purpose computer. For example, when programmed to perform the algorithms described herein, the computer processor typically acts as a special purpose bodily-emission-analysis computer processor. Typically, the operations described herein that are performed by computer processors transform the physical state of a memory, which is a real physical article, to have a different magnetic polarity, electrical charge, or the like depending on the technology of the memory that is used.

It will be appreciated by persons skilled in the art that the present disclosure is not limited to what has been particularly shown and described hereinabove. Rather, the scope of the present disclosure includes both combinations and sub-combinations of the various features described hereinabove, as well as variations and modifications thereof that are not in the prior art, which would occur to persons skilled in the art upon reading the foregoing description.

The invention claimed is:

1. An apparatus for use in conjunction with a toilet bowl into which urine of a subject and feces of the subject can be emitted and in conjunction with an output device, the apparatus comprising:

an illumination component configured to illuminate the emitted urine with light at a selected wavelength band;

one or more sensors configured to couple to the toilet bowl, detect one or more urine-related parameters relating to the emitted urine and detect one or more feces-related parameters relating to the emitted feces wherein the one or more urine-related parameters includes a first parameter being urine color and wherein the one or more sensors includes a first sensor configured to detect the urine color based on the absorption of the light at the selected wavelength band; and at least one computer processor configured to:

receive the detected one or more urine-related parameters;

identify the one or more urine-related parameters including the detected urine color;

receive the detected one or more feces-related parameters;

identify the one or more feces-related parameters;

using at least one of the identified one or more urine-related parameters including the detected urine color, determine whether the subject is dehydrated or is not dehydrated;

using at least one of the identified one or more feces-related parameters, and responsive to determining the subject is dehydrated, classify the subject with a particular dehydration; and generate an output signal indicative of the classification of the particular dehydration to the output device.

2. The apparatus of claim 1, wherein the particular dehydration is selected from the group consisting of: isotonic dehydration, hypertonic dehydration, and hypotonic dehydration.

3. The apparatus according to claim 1, wherein:

the one or more sensors includes a second sensor configured to detect urine volume; and the at least one computer processor is further configured to identify a second urine-related parameter of the one or more urine-related parameters relating to urine based on the detected urine volume.

4. The apparatus according to claim 1, wherein:

the one or more sensors includes a second sensor configured to detect urine voiding duration; and the at least one computer processor is further configured to identify a second urine-related parameter of the one or more urine-related parameters relating to urine based on the detected urine voiding duration.

5. The apparatus according to claim 1, wherein the at least one computer processor is further configured to identify the one or more feces-related parameters relating to the feces based on the detected one or more feces-related parameters selected from the group consisting of: shape, size, texture, and color.

6. The apparatus of claim 1, wherein:

the one or more sensors includes a second sensor configured to detect urine voiding frequency of the subject; and the at least one computer processor is further configured to identify a second urine-related parameter of the one or more urine-related parameters relating to the urine based on the detected urine voiding frequency.

7. The apparatus according to claim 6, wherein the at least one computer processor is configured to determine the urine voiding frequency of the subject by automatically tracking the subject is urinating at a given time.

8. The apparatus according to claim 1, wherein the at least one computer processor is further configured to identify the one or more feces-related parameters relating to the feces by computationally analyzing an image of the feces.

9. The apparatus according to claim 8, wherein the computationally analyzing comprises one or more selected from the group consisting of a masking, a contrast enhancement, an image-edge detection, a region-of-interest detection, a morphological changes application, and a segmentation.

10. The apparatus according to claim 1, wherein:

the at least one computer processor is further configured to determine the urine specific gravity from the detected urine color, and determine whether the subject is dehydrated or is not dehydrated using the determined urine specific gravity.

11. The apparatus according to claim 10, wherein:

the first sensor is further configured to detect a signal indicative of the absorption of cyan-green light by the urine; and the at least one computer processor is further configured to determine the urine specific gravity using the detected signal.

12. The apparatus according to claim 1, wherein:

the wavelength band is within a range of 440-480 nm;

the first sensor is configured to detect a first signal indicative of the light emitted by the urine at a wavelength within a range of 505-535 nm in response to the illuminating; and the at least one computer processor is further configured to determine oxidized urobilin concentration within the urine using the first signal.

13. The apparatus according to claim 12, wherein:

the one or more sensors comprises aa second sensor configured to detect a second signal indicative of the absorption of light within the wavelength band of 480-520 nm by the urine; and the at least one computer processor is further configured to determine the oxidized urobilinogen concentration within the urine using the second signal.

14. The apparatus according to claim 12, wherein the at least one computer processor is further configured to:

determine the ratio of the light absorption by the urine at the first wavelength band over light absorption by the urine at a second wavelength band; and determine bilirubin concentration within the urine using the determined ratio.

\* \* \* \* \*